(12) United States Patent
Meng et al.

(10) Patent No.: US 11,927,534 B2
(45) Date of Patent: Mar. 12, 2024

(54) SPECTROMETER AND FABRICATION METHOD THEREOF

(71) Applicant: BOE TECHNOLOGY GROUP CO., LTD., Beijing (CN)

(72) Inventors: Xianqin Meng, Beijing (CN); Xue Dong, Beijing (CN); Wei Wang, Beijing (CN); Jifeng Tan, Beijing (CN); Xiandong Meng, Beijing (CN); Xiaochuan Chen, Beijing (CN); Jian Gao, Beijing (CN); Pengxia Liang, Beijing (CN); Fangzhou Wang, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 299 days.

(21) Appl. No.: 16/633,358

(22) PCT Filed: Jul. 18, 2019

(86) PCT No.: PCT/CN2019/096571
§ 371 (c)(1),
(2) Date: Jan. 23, 2020

(87) PCT Pub. No.: WO2020/029763
PCT Pub. Date: Feb. 13, 2020

(65) Prior Publication Data
US 2021/0231565 A1    Jul. 29, 2021

(30) Foreign Application Priority Data

Aug. 8, 2018 (CN) .......................... 201810897371.2

(51) Int. Cl.
*G01N 21/64* (2006.01)
*H01L 27/15* (2006.01)
(Continued)

(52) U.S. Cl.
CPC ..... *G01N 21/6456* (2013.01); *G01N 21/6404* (2013.01); *H01L 27/156* (2013.01);
(Continued)

(58) Field of Classification Search
CPC ........... G01N 21/6456; G01N 21/6404; G01N 2021/035; G01N 21/255; G01N 21/6454;
(Continued)

(56) References Cited

U.S. PATENT DOCUMENTS

| 8,565,281 B2 | 10/2013 | Kambhampati et al. |
| 9,599,564 B1 | 3/2017 | Li |

(Continued)

FOREIGN PATENT DOCUMENTS

| CN | 201637669 | 11/2010 |
| CN | 104762085 A | 7/2015 |

(Continued)

OTHER PUBLICATIONS

Chinese Office Action dated Jul. 30, 2020 corresponding to Chinese Patent Application No. 201810897371.2; 14 pages.
(Continued)

*Primary Examiner* — Marcus H Taningco
(74) *Attorney, Agent, or Firm* — Leason Ellis LLP (57) ABSTRACT

A spectrometer and a fabrication method thereof. The spectrometer includes: a first base substrate; a second base substrate opposite to the first base substrate; a detection channel between the first base substrate and the second base substrate; a quantum dot light emitting layer on a side of the first base substrate that is close to the second base substrate, and including a plurality of quantum dot light emitting units; a black matrix on the side of the first base substrate that is close to the second base substrate, and configured to separate the plurality of quantum dot light emitting units; and a sensor layer, including a plurality of sensors, the plurality of
(Continued)

sensors being in one-to-one correspondence with the plurality of quantum dot light emitting units.

20 Claims, 5 Drawing Sheets

(51) Int. Cl.
*H01L 31/12* (2006.01)
*H01L 33/06* (2010.01)
*H01L 33/50* (2010.01)

(52) U.S. Cl.
CPC .............. *H01L 31/12* (2013.01); *H01L 33/06* (2013.01); *H01L 33/502* (2013.01); *H01L 2933/0041* (2013.01)

(58) Field of Classification Search
CPC .... G01N 21/31; G01N 21/6402; G01N 21/01; G01N 2021/0112; G01N 2223/316; H01L 27/156; H01L 31/12; H01L 33/06; H01L 33/502; H01L 2933/0041; G01J 3/0205; G01J 3/0259; G01J 3/10; G01J 3/2803; G01J 3/36; G01J 3/42
See application file for complete search history.

(56) References Cited

U.S. PATENT DOCUMENTS

| | | | |
|---|---|---|---|
| 9,867,676 B2 | 1/2018 | Ertugrul et al. | |
| 2008/0238294 A1 | 10/2008 | Xu et al. | |
| 2010/0133418 A1* | 6/2010 | Sargent | H01L 27/305 977/773 |
| 2015/0145405 A1* | 5/2015 | Yang | H05B 33/12 313/498 |
| 2016/0093677 A1 | 3/2016 | Tseng et al. | |
| 2016/0218141 A1* | 7/2016 | Cai | H01L 33/06 |
| 2016/0349183 A1* | 12/2016 | Lai | G01N 21/7746 |
| 2017/0020390 A1 | 1/2017 | Flitsch et al. | |
| 2017/0020440 A1 | 1/2017 | Flitsch et al. | |
| 2017/0086676 A1* | 3/2017 | Flitsch | G02C 7/04 |
| 2017/0090248 A1 | 3/2017 | Yoneyama et al. | |
| 2017/0119287 A1* | 5/2017 | Flitsch | A61B 3/113 |
| 2018/0120155 A1 | 5/2018 | Rosen et al. | |
| 2018/0180475 A1 | 6/2018 | Pearl, Jr. et al. | |
| 2018/0233537 A1* | 8/2018 | Liu | H01L 33/06 |
| 2019/0288160 A1* | 9/2019 | Atature | H01L 33/32 |

FOREIGN PATENT DOCUMENTS

| | | | | |
|---|---|---|---|---|
| CN | 204807458 U | | 11/2015 | |
| CN | 106768331 | | 5/2017 | |
| CN | 104515755 B | | 8/2017 | |
| CN | 107037017 A | | 8/2017 | |
| CN | 108281554 | | 7/2018 | |
| EP | 3733814 A1 | * | 11/2020 | ........... C09K 11/025 |
| JP | 2014203761 A | | 10/2014 | |
| JP | 2016000521 A | | 1/2016 | |
| JP | 2016071366 A | | 5/2016 | |
| JP | 2017023747 A | | 2/2017 | |
| JP | 2018107084 A | | 7/2018 | |
| KR | 20160111142 A | | 9/2016 | |
| WO | 2018130938 A1 | | 7/2018 | |

OTHER PUBLICATIONS

Indian Office Action in corresponding Indian Application No. 202017021671, dated Jun. 18, 2021.
Korean Office Action for corresponding Korean application No. 10-2020-7015336 and its English translation, dated Aug. 31, 2021. 20 pages.
Extended European search report for the corresponding European Patent Application No. 19847125.2, dated May 3, 2022.
Notice of Reasons for Refusal and English translation for corresponding Japanese Application No. 2020-529585, dated Aug. 1, 2023. 10 pages.

* cited by examiner

| Forming a black matrix and a quantum dot light emitting layer including a plurality of quantum dot light emitting units on a first base substrate |
|---|
| Forming a sensor layer including a plurality of sensors |
| Providing a second base substrate opposite to the first base substrate to form a detection channel between the first base substrate and the second base substrate; wherein, the quantum dot light emitting layer is located on a side of the first base substrate that is close to the second base substrate; the black matrix is located on the side of the first base substrate that is close to the second base substrate, and is configured to separate the plurality of quantum dot light emitting units; and the plurality of sensors and the plurality of quantum dot light emitting units are in one-to-one correspondence with each other |

SPECTROMETER AND FABRICATION METHOD THEREOF

CROSS-REFERENCE TO RELATED APPLICATION

The application is a U.S. National Stage Application under 35 U.S.C. § 371 of International Patent Application No. PCT/CN2019/096571, filed Jul. 18, 2019, which claims priority to the Chinese patent application No. 201810897371.2, filed Aug. 8, 2018, both of which are incorporated herein by reference in their entireties as part of the present application.

TECHNICAL FIELD

At least one example of the present disclosure relates to a spectrometer and a fabrication method thereof.

BACKGROUND

As an analytical instrument, a spectrometer is widely applied to various scientific fields, and is especially one of most important observation means in physical, chemical and biological research.

SUMMARY

At least one embodiment of the disclosure is related to a spectrometer and fabrication method thereof.

At least one embodiment of the disclosure provides a spectrometer, comprising: a first base substrate; a second base substrate opposite to the first base substrate; a detection channel between the first base substrate and the second base substrate; a quantum dot light emitting layer on a side of the first base substrate that is close to the second base substrate, and including a plurality of quantum dot light emitting units; a black matrix on the side of the first base substrate that is close to the second base substrate, and configured to separate the plurality of quantum dot light emitting units; and a sensor layer, including a plurality of sensors in one-to-one correspondence with the plurality of quantum dot light emitting units.

In some examples, the black matrix is configured to form a plurality of accommodating spaces each of which is configured to accommodate one of the plurality of quantum dot light emitting units; and in a direction perpendicular to the first base substrate, the black matrix has a size larger than or equal to that of the quantum dot light emitting layer.

In some examples, the spectrometer further comprises a protective layer on a side of the quantum dot light emitting layer that is away from the first base substrate, wherein the protective layer is configured to protect the quantum dot light emitting layer.

In some examples, in the direction perpendicular to the first base substrate, a sum of sizes of the protective layer and the quantum dot light emitting layer is larger than or equal to the size of the black matrix.

In some examples, the quantum dot light emitting layer is formed by adopting at least one selected from the group consisting of quantum dots of different types and quantum dots of different sizes.

In some examples, the sensor layer is on a side of the detection channel that is away from the quantum dot light emitting layer, and an orthogonal projection of the sensor layer on the first base substrate falls within an orthogonal projection of the quantum dot light emitting layer on the first base substrate.

In some examples, the sensor layer is on a side of the detection channel that is close to the quantum dot light emitting layer, and an orthogonal projection of the sensor layer on the first base substrate falls within an orthogonal projection of the black matrix on the first base substrate.

In some examples, the spectrometer further comprises a light source portion configured to provide excitation light irradiated onto the quantum dot light emitting layer to excite the quantum dot light emitting layer to emit light.

In some examples, the light source portion is on a side of the first base substrate that is away from the second base substrate, and includes a backlight of direct-lit type; and a reflective layer is provided on a side of the backlight of direct-lit type that is close to the first base substrate.

In some examples, the light source portion is on a side of the first base substrate that is away from the second base substrate, and includes a backlight of edge-lit type; and a reflective layer is provided on a side of the backlight of the edge-lit type that is away from the first base substrate.

In some examples, the light source portion includes a light source on a side face of the first base substrate; the first base substrate is a glass substrate and constitutes an optical waveguide; the first base substrate further includes a plurality of light extraction structures in one-to-one correspondence with the plurality of quantum dot light emitting units; and the plurality of light extraction structures are located on the side of the first base substrate that is close to the second base substrate.

In some examples, the light extraction structure includes a blind hole.

In some examples, the spectrometer further comprises a first electrode on a side of the quantum dot light emitting units that is away from the second base substrate and a second electrode on a side of the quantum dot light emitting unit that is close to the second base substrate; and the first electrode and the second electrode are configured to be applied with different voltages to excite the quantum dot light emitting units to emit light.

In some examples, the black matrix is located between the first electrode and the second electrode.

In some examples, the second electrode includes a portion within the accommodating space.

In some examples, the orthogonal projection of the quantum dot light emitting layer on the first base substrate falls within an orthogonal projection of the detection channel on the first base substrate.

At least one embodiment of the disclosure provides a fabrication method of a spectrometer, comprising: forming a black matrix and a quantum dot light emitting layer including a plurality of quantum dot light emitting units on a first base substrate; forming a sensor layer including a plurality of sensors; and providing a second base substrate opposite to the first base substrate to form a detection channel between the first base substrate and the second base substrate, wherein the quantum dot light emitting layer is on a side of the first base substrate that is close to the second base substrate; the black matrix is on the side of the first base substrate that is close to the second base substrate, and is configured to separate the plurality of quantum dot light emitting units; and the plurality of sensors and the plurality of quantum dot light emitting units are in one-to-one correspondence with each other.

In some examples, forming the black matrix and the quantum dot light emitting layer including the plurality of quantum dot light emitting units on the first base substrate includes: forming the black matrix including a plurality of accommodating spaces on the first base substrate; and dripping a quantum dot solution into each of the plurality of accommodating spaces, heating to remove a substance to be removed from the quantum dot solution, to obtain the quantum dot light emitting layer.

In some examples, dripping the quantum dot solution into each of the plurality of accommodating spaces includes: forming a solution of quantum dots that can be excited to generate light of different wavelengths, and dripping the solution of quantum dots that can be excited to generate light of different wavelengths into the respective corresponding accommodating spaces.

In some examples, after the quantum dot solution is dripped into each of the plurality of accommodating spaces, the substance to be removed is removed from the quantum dot solution by a single heating process.

BRIEF DESCRIPTION OF THE DRAWINGS

In order to clearly illustrate the technical solution of the embodiments of the invention, the drawings of the embodiments will be briefly described in the following; it is obvious that the described drawings are only related to some embodiments of the invention and thus are not limitative of the invention.

DETAILED DESCRIPTION

In order to make objects, technical details and advantages of the embodiments of the invention apparent, the technical solutions of the embodiment will be described in a clearly and fully understandable way in connection with the drawings related to the embodiments of the invention. It is obvious that the described embodiments are just a part but not all of the embodiments of the invention. Based on the described embodiments herein, those skilled in the art can obtain other embodiment(s), without any inventive work, which should be within the scope of the invention.

Unless otherwise defined, all the technical and scientific terms used herein have the same meanings as commonly understood by one of ordinary skill in the art to which the present disclosure belongs. The terms "first," "second," etc., which are used in the present disclosure, are not intended to indicate any sequence, amount or importance, but distinguish various components. Also, the terms "comprise," "comprising," "include," "including," etc., are intended to specify that the elements or the objects stated before these terms encompass the elements or the objects and equivalents thereof listed after these terms, but do not preclude the other elements or objects. The phrases "connect", "connected", etc., are not intended to define a physical connection or mechanical connection, but may include an electrical connection, directly or indirectly. "On," "under," "right," "left" and the like are only used to indicate relative position relationship, and when the position of the object which is described is changed, the relative position relationship may be changed accordingly.

Quantum dots are semiconductor crystals whose sizes are adjustable and can be scaled to an order of several nanometers, which are sensitive to light or electricity, and may be excited by light or electricity to emit light.

Quantum dots are nanoscale semiconductor crystals, whose three-dimensional sizes are all below 100 nanometers. Quantum dots have a quantum effect: when fabricated as small as a nanometer scale, these semiconductor crystals of different sizes may emit light of different colors, even if they differ in size by a few or a dozen atoms. By adjusting a size of a quantum dot, light of a desired wavelength (color) may be obtained.

A quantum dot solution obtained by putting quantum dots into a dispersion has dual properties of a crystal and a solution. A quantum dot has a size that is adjustable, and only consists of a few atoms, which confines its activities within a limited scope, and deprives it of original semiconductor characteristics. Also because its activities are confined within a narrow space, light emission is easily stimulated by affecting its energy state.

By using quantum dots, a volume of a spectrometer can be reduced without affecting resolution, application range and efficiency thereof. Using a quantum dot material is one of effective methods to overcome design limitations of a common miniature spectrometer.

Figure 1:
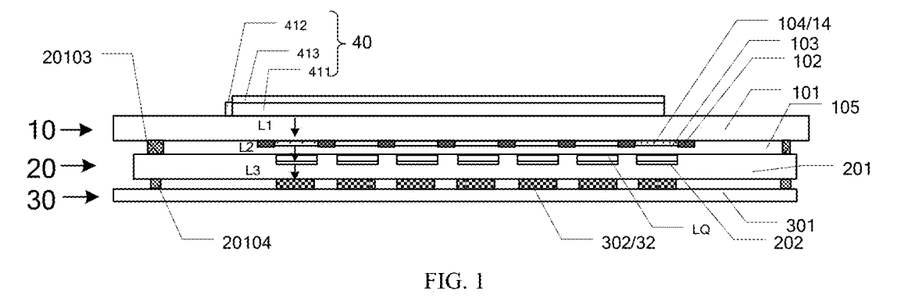
FIG. 1 is a cross-sectional view of a spectrometer provided by an example of the present disclosure.

FIG. 1 is a cross-sectional view of a spectrometer provided by an example of the present disclosure. As shown in FIG. 1, the spectrometer comprises a first substrate 10, a second substrate 20 and a third substrate 30. The first substrate 10 includes a first base substrate 101, a black matrix 102 and a quantum dot light emitting layer 14. The second substrate 20 includes a second base substrate 201 and a detection channel 202. The third substrate 30 includes a third base substrate 301 and a sensor layer 32. The first substrate 10 and the second substrate 20 are provided opposite to each other, and the second substrate 20 and the third substrate 30 are provided opposite to each other. The second base substrate 201 and the first base substrate 101 are provided opposite to each other. The second base substrate 201 and the third base substrate 301 are provided opposite to each other. For example, as shown in FIG. 1, the sensor layer 32 is located on a side of the second base substrate 201 that is away from the first base substrate 101. For example, as shown in FIG. 1, the sensor layer 32 is located on a side of the third base substrate 301 that is close to the second base substrate 201. For example, as shown in FIG. 1, the detection channel 202 is located between the quantum dot light emitting layer 14 and the sensor layer 32.

As shown in FIG. 1, the detection channel 202 is located between the first base substrate 101 and the second base substrate 201. The quantum dot light emitting layer 14 is located on a side of the first base substrate 101 that is close to the second base substrate 201. The quantum dot light emitting layer 14 includes a plurality of quantum dot light emitting units 104. The black matrix 102 is located on the side of the first base substrate 101 that is close to the second base substrate 201. The black matrix 102 is configured to separate the plurality of quantum dot light emitting units 104. The sensor layer 32 includes a plurality of sensors 302. The plurality of sensors 302 and the plurality of quantum dot light emitting units 104 are in one-to-one correspondence with each other.

For example, the detection channel 202 is configured to accommodate or pass a liquid LQ to be detected. For example, each of the plurality of quantum dot light emitting units 104 is configured to emit light to irradiate the liquid LQ to be detected. For example, a sensor 302 may include an optical sensor. For example, each of the plurality of sensors 302 may be configured to receive light emitted by the quantum dot light emitting layer for detection, but is not limited thereto. For example, in order to facilitate irradiation of the light emitted by the quantum dot light emitting layer 14 onto the liquid LQ to be detected, the detection channel 202 at least includes a portion corresponding to the quantum dot light emitting layer 14. For example, the detection channel 202 at least includes a portion corresponding to the plurality of quantum dot light emitting units 104. For example, an orthogonal projection of the quantum dot light emitting layer 14 on the first base substrate 101 falls within an orthogonal projection of the detection channel 202 on the first base substrate 101. That is, an orthogonal projection of the plurality of quantum dot light emitting units 104 in the quantum dot light emitting layer 14 on the first base substrate 101 falls within the orthogonal projection of the detection channel 202 on the first base substrate 101. That is, the orthogonal projection of the plurality of quantum dot light emitting units 104 in the quantum dot light emitting layer 14 on the first base substrate 101 is smaller than or equal to the orthogonal projection of the detection channel 202 on the first base substrate 101.

In at least one example of the present disclosure, on the one hand, miniaturization of the spectrometer may be implemented by using a quantum dot layer to emit light; on the other hand, the black matrix 102 may function to isolate different quantum dot light emitting units, which may avoid light emitted by adjacent quantum dot light emitting units from affecting light irradiated onto the sensor 302, so as to avoid influence on a detection result, and facilitates improvement of detection accuracy.

For example, the black matrix is usually used in a color display device and is an opaque portion among trichromatic (e.g., R, G, B) patterns. For example, the black matrix may be a photoresist containing a black dye, but is not limited thereto.

For example, the liquid to be detected may have operations such as droplet transportation, divergence and confluence, and reaction performed in the detection channel 202. For example, the liquid to be detected may be passed into the detection channel 202, and the liquid to be detected may be a liquid obtained by subjecting a liquid passed into the detection channel 202 to a reaction in the detection channel 202, which will not be limited in the examples of the present disclosure. For example, the detection channel 202 is a microchannel. For example, the second substrate 20 may be a microfluidic device. An arrangement mode of the detection channel is not limited to that shown in FIG. 1.

In some examples, in order to make different quantum dot light emitting units emit light of different wavelengths, the quantum dot light emitting layer 14 is formed by quantum dots of different types, quantum dots of different sizes, or quantum dots of different types and different sizes. In this case, the black matrix 102 may also prevent a crosstalk problem of light emitted by quantum dots that emit light of different wavelengths.

In some examples, the quantum dot light emitting layer 14 emits light to form a spectrum. The quantum dot light emitting layer 14 may form light of various wavelength bands (wavelengths), for example, it may form a continuous spectrum from ultraviolet to infrared, but it is not limited thereto.

The quantum dots may by excited to emit light of different wavelengths by changing a size or a material thereof, which may implement a continuous spectrum from ultraviolet to infrared, and facilitate obtaining a wide spectrum. The use of the quantum dot material in the spectrometer can reduce a volume of the spectrometer without affecting resolution, application range and efficiency thereof. At a same time, quantum dots may be dispersed in a solvent and processed in a liquid form.

For example, quantum dots of different sizes can exhibit fluorescence of different colors when excited by excitation light such as laser. In the examples of the present disclosure, the excitation light is not limited to laser.

For example, the quantum dot material may include at least one of CdS, CdSe and ZnS, but it is not limited thereto, as long as it is a quantum dot that can emit light of different wavelengths through size adjustment.

For example, cadmium selenide quantum dots of different sizes may be excited by ultraviolet laser to display fluorescence of different colors. For example, semiconductor nanocrystalline cadmium selenide (CdSe) emits blue light at 2 nanometers and red light at 8 nanometers, as well as green light, yellow light and orange light, etc. at sizes therebetween.

As shown in FIG. 1, in some examples, the black matrix 102 is configured to form a plurality of accommodating spaces 103; each of the plurality of accommodating spaces 103 is configured to accommodate one of the plurality of quantum dot light emitting units 104; in a direction perpendicular to the first base substrate 101, a size of the black matrix 102 is larger than or equal to a size of the quantum dot light emitting layer 14. A quantum dot light emitting unit 104 is formed within an accommodating space 103, which facilitates fabrication of the quantum dot light emitting layer.

For example, in the direction perpendicular to the first base substrate 101, the size of the black matrix 102 may be on an order of micrometers. For example, in the direction perpendicular to the first base substrate 101, the size of the black matrix 102 may be 2 μm to 3 μm. For example, the size of the black matrix 102 in the direction perpendicular to the first base substrate 101 is just the size of the accommodating space 103. For example, in the examples of the present disclosure, a size of a certain element/component in the direction perpendicular to the first base substrate 101 refers to a thickness of the element/component in the direction perpendicular to the first base substrate 101.

For example, the accommodating space 103 may be generally scaled to an order of several hundred nanometers to micrometers, which, thus, may facilitate miniaturization of the spectrometer. For example, a length or a width of the accommodating space 103 is on an order of several hundred nanometers to micrometers. For example, in the direction perpendicular to the first base substrate 101, the size of the accommodating space is 2 μm to 3 μm.

As shown in FIG. 1, in some examples, in order to facilitate the fabrication of the quantum dot light emitting layer, in the direction perpendicular to the first base substrate 101, the size of the accommodating space 103 is larger than or equal to the size of the quantum dot light emitting layer 14. For example, if sizes of the quantum dot light emitting layers 14 in different accommodating spaces are different, the size of the accommodating space 103 is larger than or equal to a size of a largest quantum dot light emitting layer 14.

For example, in the direction perpendicular to the first base substrate 101, a ratio of the size of the quantum dot light emitting layer 14 to the size of the accommodating space 103 may be 90% to 98%. Further, for example, in the direction perpendicular to the first base substrate 101, the ratio of the size of the quantum dot light emitting layer 14 to the size of the accommodating space 103 is 93% to 95%.

For example, the first base substrate 101 and the third base substrate 301 may be base substrates of a liquid crystal display (LCD) or an organic light emitting diode (OLED) display. For example, the first base substrate 101 and the third base substrate 301 may be transparent substrates, such as glass substrates, or may also be resin substrates, etc. For example, the first base substrate 101 and the third base substrate 301 may be made of optical glass. As compared with a silicon wafer or other organic substrates, a glass substrate is more favorable for fabricating the spectrometer, and more favorable for cost reduction and mass production.

For example, thicknesses of the first base substrate 101 and the third base substrate 301 may both be 0.1 mm to 2 mm, which may be determined by specific product design or process conditions. For example, upper and lower surfaces of the first base substrate 101 and/or the third base substrate 301 may have better flatness and parallelism to facilitate fabrication of the first substrate 10 and/or the third substrate 30.

For example, as shown in FIG. 1, light L3, which is formed after light L2 emitted by a quantum dot light emitting unit 104 passes through the liquid to be detected, can be sensed by a sensor 302 at a corresponding position; and light of different wavelengths is detected and labelled with respect to different substances at different positions in the liquid to be detected in the channel, such that multiple wavelengths and multiple substances (molecules) can be detected and labelled quickly and precisely all at once.

For example, the sensor 302 is a photosensitive detector. For example, the optical sensor 302 may be at least one of a charge coupled device (CCD), a complementary metal oxide semiconductor (CMOS), a PIN diode, or the like, which will not be limited in the examples of the present disclosure.

As shown in FIG. 1, in some examples, the sensor 302 is configured to detect light irradiated thereon; and the light irradiated onto the sensor 302 may be transmitted light after the light emitted by the quantum dot light emitting unit 104 passes through the liquid LQ to be detected, or may also be light emitted by the liquid in the detection channel 202 as irradiated with the light emitted by the quantum dot light emitting unit 104, but it is not limited thereto. When it is to show whether there is a liquid passing through the detection channel, or when different types of liquids pass through the detection channel, the sensor 302 may output a corresponding electrical signal to implement a detection purpose.

As shown in FIG. 1, in some examples, the sensor layer 32 is located on a side of the detection channel 202 that is away from the quantum dot light emitting layer 14. In order to facilitate the sensor 302 to obtain light irradiated thereon, an orthogonal projection of the sensor layer 32 on the first base substrate 101 falls within the orthogonal projection of the quantum dot light emitting layer 14 on the first base substrate 101. For example, an orthogonal projection of a quantum dot light emitting unit 104 in each accommodating space 103 on the first base substrate 101 coincides with an orthogonal projection of a sensor 302 corresponding to the accommodating space 103 on the first base substrate 101. For example, the orthogonal projection of the plurality of quantum dot light emitting units 104 on the first base substrate 101 coincide with an orthogonal projection of the plurality of sensors 302 on the first base substrate 101.

As shown in FIG. 1, in some examples, the spectrometer further comprises a protective layer 105 located on a side of the quantum dot light emitting layer 14 that is away from the first base substrate 101. The protective layer 105 is configured to protect the quantum dot light emitting layer 14. The protective layer 105 mainly functions to isolate the quantum dot light emitting units and protect the quantum dot light emitting units from being polluted, and meanwhile, realize the surface planarization. For example, the protective layer 105 may be made of an epoxy resin-based or acrylic resin-based polymer material. For example, the protective layer 105 may serve as a package layer. The protective layer 105 may cover the plurality of quantum dot light emitting units 104.

As shown in FIG. 1, in some examples, in the direction perpendicular to the first base substrate 101, a sum of sizes of the protective layer 105 and the quantum dot light emitting layer 14 is larger than or equal to the size of the accommodating space 103. In a case where the sum of the sizes of the protective layer 105 and the quantum dot light emitting layer 14 is larger than the size of the accommodating space 103, a surface of the protective layer 105 that is away from the first base substrate 101 is a flat surface, which may facilitate fabricating the protective layer 105, improving a protective effect of the protective layer 105, and reducing defects such as faults in the protective layer 105. In a case where the sum of the sizes of the protective layer 105 and the quantum dot light emitting layer 14 is equal to the size of the accommodating space 103, a portion within the accommodating space 103 other than the quantum dot light emitting unit 104 is filled by the protective layer 105. Protective layers 105 located in different accommodating spaces 103 are discontinuous.

As shown in FIG. 1, in some examples, the spectrometer further comprises a light source portion 40 located on a side of the first base substrate 101 that is away from the second base substrate 201. The light source portion 40 is located on a side opposite to the side of the first base substrate 101 that is provided with the black matrix 102 and the quantum dot light emitting layer 14. The light source portion 40 is configured to provide excitation light irradiated onto the quantum dot light emitting layer to excite the quantum dot light emitting layer to emit light. The black matrix 102 may prevent background light leakage, improve display contrast, prevent color mixing, and increase color purity.

As shown in FIG. 1, in some examples, the light source portion 40 includes a backlight substrate 411 and a light source 412 located on one side of the backlight substrate 411; and light emitted by the light source 412 enters the backlight substrate 411, converted into an area light source, and then is emitted toward the quantum dot light emitting layer 14 to excite the quantum dot light emitting layer 14 to emit light. For example, the backlight substrate 411 is a light guide plate. For example, the backlight substrate 411 is made of a transparent material. For example, a reflective layer 413 is provided on a side of the backlight substrate 411 that is away from the first base substrate 101. The arrangement of the reflective layer 413 is favorable for improving a utilization rate of light emitted by the light source 412. A material of the reflective layer 413 may include a metal. For example, the material of the reflective layer 413 may be silver.

As shown in FIG. 1, in some examples, the light source portion 40 is located on the side of the first base substrate 101 that is away from the second base substrate 201, and includes a backlight of edge-lit type; and the reflective layer 413 is provided on one side of the backlight of edge-lit type that is away from the first base substrate 101.

For example, the light source portion 40 may adopt a collimated light source; but of course, it may also not adopt a collimated light source. The examples of the present disclosure are not very strict about collimation requirements on the light source portion 40. For example, the light source portion 40 may generate ultraviolet light, but it is not limited thereto.

For example, in order to make better use of the light emitted by the quantum dot light emitting layer, the second substrate 20 is in contact with the first substrate 10. For example, in order to facilitate the sensor to better detect light irradiated thereon, the third substrate 30 is in contact with the second substrate 20. The light irradiated onto the sensor 302 may be light emitted by the quantum dot light emitting unit 104 and then passing through the liquid to be detected. For example, the light passing through the liquid to be detected may be light emitted by the quantum dot light emitting unit 104 or light emitted by a substance in the liquid to be detected as irradiated by the light emitted by the quantum dot light emitting unit 104, but it is not limited thereto.

For example, as shown in FIG. 1, a distance between the first substrate 10 and the second substrate 20 may depend on accuracy of a light emission direction of the quantum dot light emitting layer; for example, the first substrate 10 and the second substrate 20 may be closely adhered to each other.

For example, as shown in FIG. 1, the sensor 302 and the accommodating space 103 (light exit) are in one-to-one correspondence with each other; a distance between the second substrate 20 and the third substrate 30 depends on a signal-to-noise ratio requirement of the sensor 302; and the second substrate 20 and the third substrate 30 may be closely adhered to each other. For example, the third substrate 30 may be provided thereon with a buffer film layer, etc.

For example, as shown in FIG. 1, the first substrate 10 and the second substrate 20 are packaged together by a first sealant 20103; and the second substrate 20 and the third substrate 30 are packaged together by a second sealant 20104.

For example, as shown in FIG. 1, the black matrix 102 and the quantum dot light emitting layer 14 are fabricated on the first base substrate 101; the sensor layer 32 is fabricated on the third base substrate 301; and the detection channel 202 is fabricated on the second base substrate 201, which is taken as an example for description in FIG. 1. The sensor layer 32 and the detection channel 202 may also be arranged in other ways, which will be described later in conjunction with FIG. 4B and FIG. 4C.

Figure 2:
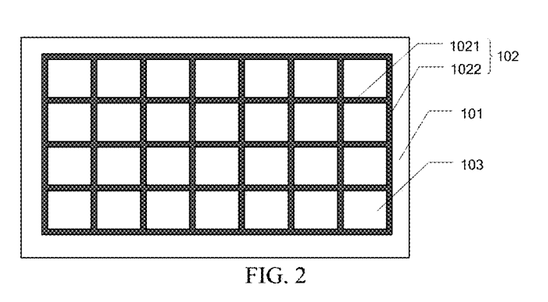
FIG. 2 is a schematic plan view of a black matrix in a first substrate in a spectrometer provided by an example of the present disclosure.

FIG. 2 is a schematic plan view of a black matrix in a spectrometer provided by an example of the present disclosure. As shown in FIG. 2, the black matrix 102 is located on the first base substrate 101; and the black matrix 102 includes a plurality of lateral black matrices 1021 and a plurality of longitudinal black matrices 1022. The plurality of lateral black matrices 1021 and the plurality of longitudinal black matrices 1022 intersect with each other laterally and longitudinally to form the plurality of accommodating spaces 103. Each accommodating space 103 may be regarded as a container for containing a quantum dot solution or a quantum dot light emitting unit.

Figure 3A:
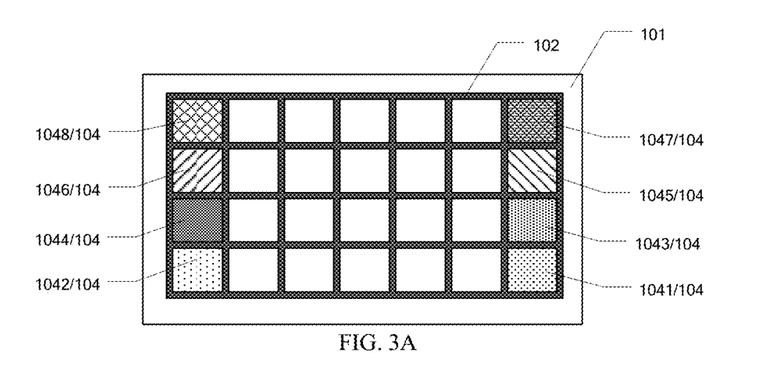
FIG. 3A is a schematic plan view of a first substrate in a spectrometer provided by an example of the present disclosure.

FIG. 3A is a schematic plan view of a first substrate in a spectrometer provided by an example of the present disclosure. As shown in FIG. 3A, the plurality of quantum dot light emitting units 104 may be arranged in an array, including a plurality of rows and a plurality of columns. In FIG. 3A, it is illustrated with an array of four rows and seven columns as an example, but the array may also have other structures. For example, areas of respective quantum dot light emitting units 104 may be equal to one another, but it is not limited thereto. The first substrate 10 may also include quantum dot light emitting units 104 having unequal areas. For example, each quantum dot light emitting unit 104 may emit light of one color, and the plurality of quantum dot light emitting units 104 may emit a continuous spectrum.

For example, as shown in FIG. 3A, the plurality of quantum dot light emitting units 104 may include a first quantum dot light emitting unit 1041, a second quantum dot light emitting unit 1042, a third quantum dot light emitting unit 1043, a fourth quantum dot light emitting unit 1044, a fifth quantum dot light emitting unit 1045, a sixth quantum dot light emitting unit 1046, a seventh quantum dot light emitting unit 1047, and an eighth quantum dot light emitting unit 1048 that respectively emit light of different wavelengths.

Figure 3B:
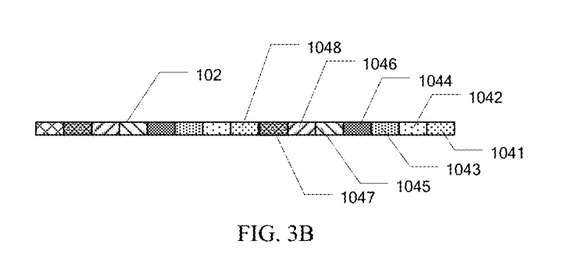
FIG. 3B is a schematic plan view of a first substrate in a spectrometer provided by another example of the present disclosure.

FIG. 3B is a schematic plan view of a first substrate in a spectrometer provided by another example of the present disclosure. As shown in FIG. 3B, the first substrate may also be fabricated to contain only one row of accommodating spaces; similarly, the first substrate only contains one row of quantum dot light emitting units, which may also be arranged in other ways according to actual needs to achieve different detection purposes.

The spectrometer provided by the examples of the present disclosure is not limited to adopt the above-described light source portion of a unilateral-lit type, and it may also adopt a bilateral-lit type, or may also adopt a backlight of a direct-lit type.

Figure 4A:
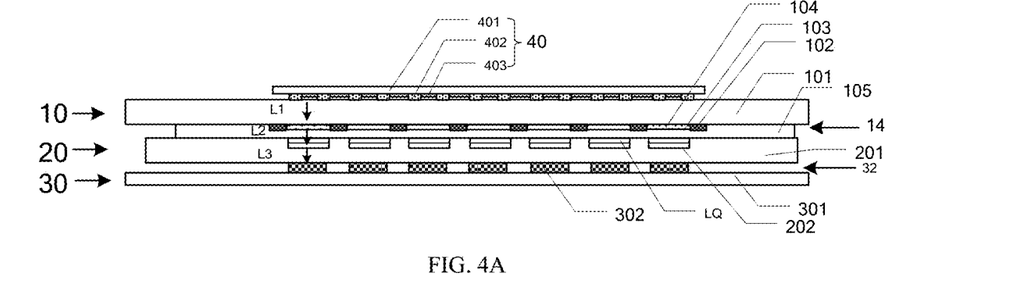
FIG. 4A is a schematic cross-sectional view of a spectrometer provided by an example of the present disclosure.

FIG. 4A is a schematic cross-sectional view of a spectrometer provided by another example of the present disclosure. For example, the light source portion 40 adopts a backlight of a direct-lit type.

As shown in FIG. 4A, in some examples, the light source portion 40 is located on the side of the first base substrate 101 that is away from the second base substrate 201; the light source portion 40 is a backlight of a direct-lit type; and a reflective layer 403 is provided on a side of the backlight of the direct-lit type that is close to the first base substrate 101.

For example, as shown in FIG. 4A, the light source portion 40 includes a backlight substrate 401 and a plurality of light sources 402 located on a side of the backlight substrate 401 that is close to the first base substrate 101. For example, a light source 402 may include a light emitting diode (LED) chip, but it is not limited thereto. A reflective layer 403 may be provided between adjacent light sources 402 of the backlight substrate 401. The arrangement of the reflective layer 403 is favorable for improving a utilization rate of light. A material of the reflective layer 413 may include a metal. For example, the material of the reflective layer 413 may be silver. For example, as shown in FIG. 4A, uniform planar light is incident from the light source portion 40 downwardly.

In the above-described spectrometer, the detection channel 202 is located between the first base substrate 101 and the second base substrate 201 in a form of being located in the second base substrate 201. In other examples of the present disclosure, the detection channel 202 may be located between the first substrate 10 and the second substrate 20, that is, the detection channel 202 is located between the base substrate 101 and the second base substrate 201 in a form of being located in a space between the first substrate 10 and the second substrate 20.

Figure 4B:
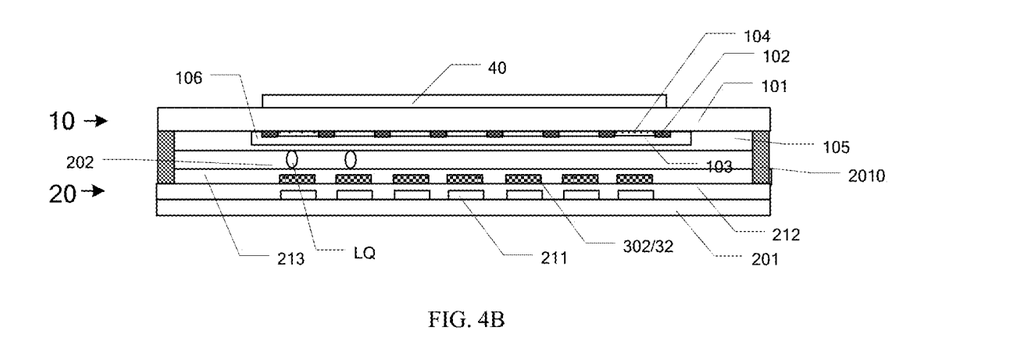
FIG. 4B is a schematic cross-sectional view of a spectrometer provided by an example of the present disclosure.

FIG. 4B is a schematic cross-sectional view of a spectrometer provided by another example of the present disclosure. The detection channel 202 is located between the first base substrate 101 and the second base substrate 201. The liquid LQ to be detected may be a droplet. A first driving electrode 106 may be provided on the first base substrate 101, and a plurality of second driving electrodes 211 may be provided on the second base substrate 201. For example, the first driving electrode 106 may be a plate-shaped electrode, and the plurality of second driving electrodes 211 may be arranged in an array. The plurality of second driving electrodes 211 may be respectively input with electrical signals. An electric field may be formed between the first driving electrode 106 and the second driving electrode 211 to drive a droplet therebetween to perform operations such as movement, divergence and confluence, and reaction, so as to let the liquid LQ to be detected pass through the detection channel 202. The sensor 302 may output a corresponding electrical signal by detecting light irradiated thereon. As shown in FIG. 4B, the light emitted by the quantum dot light emitting unit may excite a fluorescent substance in the liquid LQ to be detected to emit light, and the sensor 302 is configured to detect fluorescence irradiated thereon so as to output a detection signal.

For example, whether an actual motion trajectory of the liquid/droplet to be detected is the same as a preset trajectory may be learned by detecting a change in capacitance between the first driving electrode 106 and the plurality of second driving electrodes 211; and if the actual motion trajectory is different from the preset trajectory, an electrical signal such as a voltage on the first driving electrode 106 and the plurality of second driving electrodes 211 may be adjusted in real time to make the liquid/droplet to be detected return to the preset trajectory. Thereby, the motion trajectory of the liquid/droplet to be detected may be controlled in real time.

As shown in FIG. 4B, the first substrate 10 and the second substrate 20 may be packaged together by a sealant 2010. An insulating layer 212 may be further provided between the sensor layer 32 and the second driving electrode 211. A transparent insulating layer 213 may be further provided on a side of the sensor layer 32 that is away from the second base substrate 202.

For example, in the spectrometer shown in FIG. 4B, in order to facilitate the sensor 302 to obtain light irradiated thereon, the orthogonal projection of the sensor layer 32 on the first base substrate 101 falls within the orthogonal projection of the quantum dot light emitting layer 14 on the first base substrate 101. For example, an orthogonal projection of a quantum dot light emitting unit 104 in each accommodating space 103 on the first base substrate 101 coincides with an orthogonal projection of a sensor 302 corresponding to the accommodating space 103 on the first base substrate 101. For example, the orthogonal projection of the plurality of quantum dot light emitting units 104 on the first base substrate 101 coincides with the orthogonal projection of the plurality of sensors 302 on the first base substrate 101.

As shown in FIG. 4B, the sensor layer 32 may be located on a side of the second base substrate 201 that is close to the first base substrate 101, and the sensor layer 32 may be fabricated on the second base substrate 201.

In the above-described example, the sensor layer 32 is located on a side of the detection channel 202 that is away from the quantum dot light emitting layer 14. That is, the quantum dot light emitting layer 14 and the sensor layer 32 are located on opposite sides of the detection channel 202. However, the examples of the present disclosure are not limited thereto. In other examples, the sensor layer 32 may also be located on a side of the detection channel 202 that is close to the quantum dot light emitting layer 14.

Figure 4C:
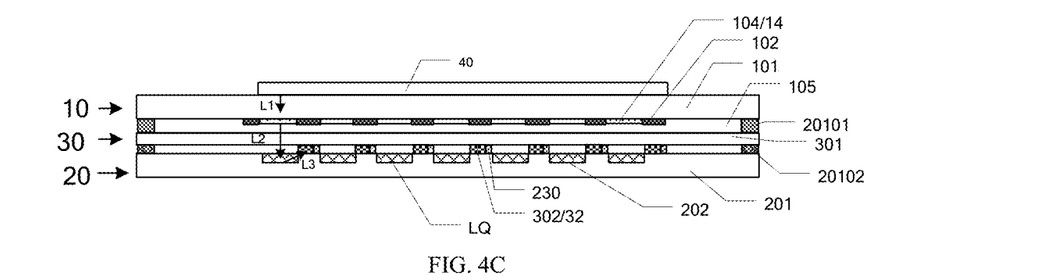
FIG. 4C is a schematic cross-sectional view of a spectrometer provided by an example of the present disclosure.

FIG. 4C is a schematic cross-sectional view of a spectrometer provided by another example of the present disclosure. As shown in FIG. 4C, the sensor layer 32 is located on the side of the detection channel 202 that is close to the quantum dot light emitting layer 14. That is, the sensor layer 32 and the quantum dot light emitting layer 14 are located on a same side of the detection channel 202. As shown in FIG. 4C, the sensor layer 32 and the quantum dot light emitting layer 14 are located on an upper side of the detection channel 202. The orthogonal projection of the sensor layer 32 on the first base substrate 101 falls within an orthogonal projection of the black matrix 102 on the first base substrate 101. For example, the orthogonal projection of the sensor layer 32 on the first base substrate 101 falls within the orthogonal projection of the black matrix 102 on the first base substrate 101, which refers to that an area of the orthogonal projection of the sensor layer 32 on the first base substrate 101 is smaller than or equal to an area of the orthogonal projection of the black matrix 102 on the first base substrate 101.

As shown in FIG. 4C, the orthogonal projection of the sensor layer 32 on the first base substrate 101 and the orthogonal projection of the quantum dot layer 14 on the first base substrate 101 do not overlap with each other.

As shown in FIG. 4C, the black matrix 102 and the quantum dot light emitting layer 14 are fabricated on the first base substrate 101; the sensor layer 32 is fabricated on the third base substrate 301; and the detection channel 202 is fabricated in the second base substrate 201. As shown in FIG. 4C, the third base substrate 301 is located between the first base substrate 101 and the second base substrate 201. It should be noted that, the example of the present disclosure is not limited to that shown in FIG. 4C. For example, the sensor layer 32 may also be fabricated on the first base substrate 101, so that the third base substrate 301 may be omitted and a thickness of the spectrometer may be further reduced.

As shown in FIG. 4C, light L1 emitted from the light source portion 40 is irradiated onto the quantum dot light emitting unit 104, the quantum dot light emitting unit 104 is excited to emit light, emitted light L2 is irradiated onto the liquid LQ to be detected in the detection channel 202, and light reflected by the liquid LQ to be detected or emitted light L3 reaches the sensor 302 corresponding to the quantum dot light emitting unit 104. With respect to cases where there is a liquid or there is no liquid passed through the detection channel 202, the sensor 302 senses that light irradiated thereon is different. With respect to cases where there are different types of liquid passed through the detection channel 202, the sensor 302 senses that light irradiated thereon is different, and thus, the sensor 302 may output a corresponding electrical signal.

As shown in FIG. 4C, in some examples, in order to avoid the reflected light of the liquid LQ to be detected in the adjacent detection channel 202 from affecting the detection result, a light shielding unit 230 is provided on a side of the sensor 302 that is close to a sensor 302 adjacent thereto, so that the sensor 302 can only detect reflected light in a detection channel 202 corresponding thereto. The light shielding unit 230 is configured to shield the reflected light of the adjacent detection channel 202. For example, a plurality of light shielding units 230 may be referred to as a light shielding layer. For example, the light shielding unit 230 may be made of a metal material. For example, as shown in FIG. 4C, the light shielding unit 230 is provided only on the side of the sensor 302 that is close to the sensor 302 adjacent thereto.

As shown in FIG. 4C, in some examples, the area of the orthogonal projection of the sensor layer 32 on the first base substrate 101 is smaller than the area of the orthogonal projection of the black matrix 102 on the first base substrate 101.

As shown in FIG. 4C, in some examples, in order to effectively utilize an area of a corresponding region of the black matrix, an area of an orthogonal projection of the sensor layer 32 and a light shielding unit 230 on the first base substrate 101 is equal to the area of the orthogonal projection of the black matrix 102 on the first base substrate 101.

For example, as shown in FIG. 4C, the first substrate 10 and the third substrate 30 are packaged together by a first sealant 20101, and the third substrate 30 and the second substrate 20 are packaged together by a second sealant 20102.

In the examples of the present disclosure, the light source portion may also adopt other modes. For example, light emitted by a light source such as a laser or an LED may be guided into an optical waveguide, and then the light is emergent into the quantum dot light emitting layer by using a light extraction structure.

Figure 5A:
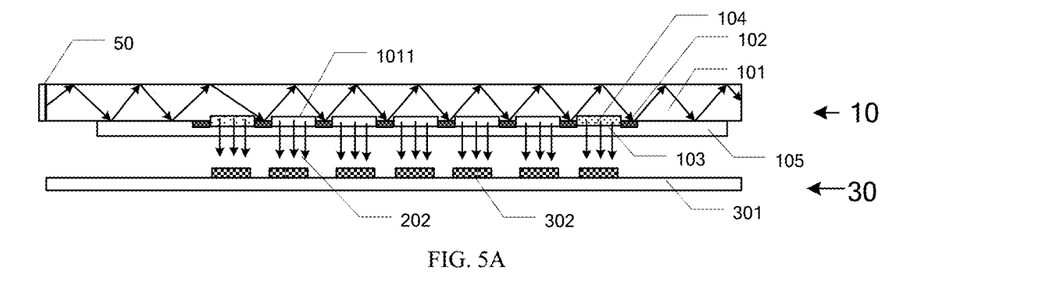
FIG. 5A is a schematic diagram of a spectrometer provided by another example of the present disclosure.

FIG. 5A is a schematic cross-sectional view of a spectrometer provided by another example of the present disclosure. As shown in FIG. 5A, the spectrometer further comprises a light source 50 located on a side face of the first base substrate 101; the first base substrate 101 is a glass substrate and constitutes an optical waveguide; the first base substrate 101 further includes a plurality of light extraction structures 1011 in one-to-one correspondence with the plurality of accommodating spaces 103; and the plurality of light extraction structures 1011 are located on the side of the first base substrate 101 that is close to the second base substrate 201. For example, except for the plurality of light extraction structures 101 that can let out light, other positions of the first base substrate 101 totally reflect light, without any emergent light. For example, the quantum dot light emitting unit 104 is also provided in the light extraction structure 1011 in addition to being provided within the black matrix.

For example, the light extraction structure includes a blind hole. For example, light is emergent from the optical waveguide as its glass surface is broken by the blind hole, and then enters the quantum dot light emitting layer, exciting the quantum dots to emit light, thereby implementing functions of the spectrometer. For example, the first base substrate 101 may be etched with the black matrix 102 as a mask to form a blind hole for emergent light. The blind hole is a non-penetrating hole. The blind hole is a groove formed by removing a portion of the first base substrate 101. The blind hole does not penetrate the first base substrate 101.

In addition to using the blind hole for light extraction, other structures such as a light extraction grating may also be used for extracting light in the optical waveguide.

In addition to photoluminescence, electroluminescence may also be adopted to make the quantum dot light emitting layer emit light. Backlight excitation or electroluminescence may be adopted to make the quantum dot light emitting layer emit light; as compared with a quantum dot photoluminescence device structure, a quantum dot electroluminescence device structure needs an additional drive structure, rather than a backlight; and for the rest of the structures, they may be mutually referred to.

The light source portion in the quantum dot photoluminescence spectrometer may be removed, and a driving structure may be formed to excite different quantum dots to emit light, so as to obtain a miniature quantum dot electroluminescence spectrometer.

Figure 5B:
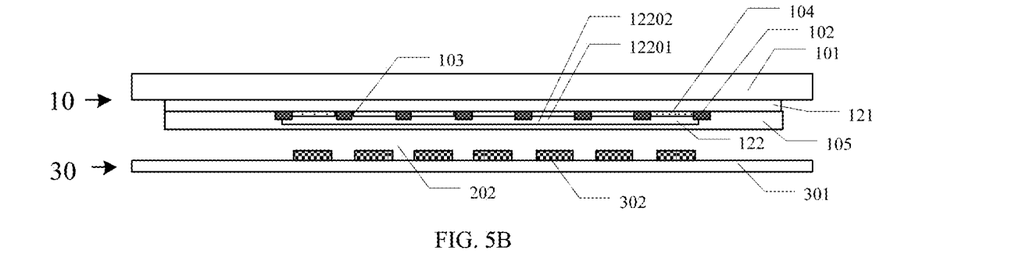
FIG. 5B is a schematic diagram of a spectrometer provided by another example of the present disclosure.

FIG. 5B is a schematic diagram of a spectrometer provided by another example of the present disclosure. As shown in FIG. 5B, the spectrometer further comprises a first electrode 121 located on a side of the quantum dot light emitting unit 104 that is away from the second base substrate 201 and a second electrode 122 located on a side of the quantum dot light emitting unit 104 that is close to the second base substrate 201; the first electrode 121 and the second electrode 122 are configured to be applied with different voltages to excite the quantum dot light emitting unit 104 to emit light. For example, the first electrode 121 and the second electrode 122 are located on the first base substrate 101 and are separately provided on both sides of the quantum dot light emitting unit 104.

As shown in FIG. 5B, in some examples, the first electrode 121 is closer to the first base substrate 101 than the second electrode 122; and the black matrix 102 is located on a side of the first electrode 121 that is away from the first base substrate 101. For example, as shown in FIG. 5B, the second electrode 122 is located on a side of the black matrix 102 that is close to the second substrate 201.

As shown in FIG. 5B, in some examples, the black matrix 102 is located between the first electrode 121 and the second electrode 122. In FIG. 5B, it is illustrated with formation of a plate-shaped first electrode 121 and a plate-shaped second electrode 122 as an example. However, shapes of the first electrode 121 and the second electrode 122 are not limited thereto.

Figure 5C:
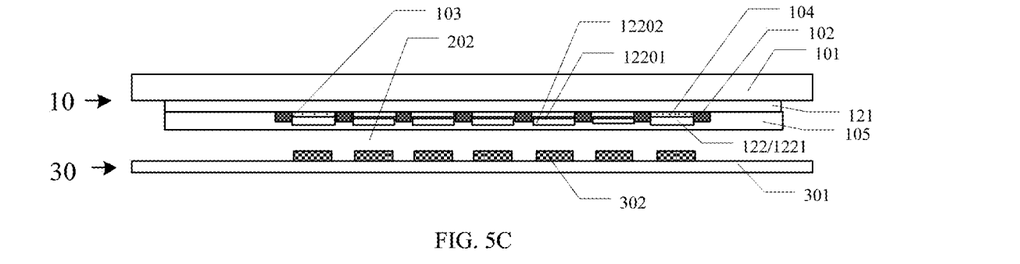
FIG. 5C is a schematic diagram of a spectrometer provided by another example of the present disclosure.

FIG. 5C is a schematic diagram of a spectrometer provided by another example of the present disclosure. The second electrode 122 includes a plurality of sub-electrodes 1221 insulated from each other, so as to respectively drive quantum dot light emitting units in different accommodating spaces to emit light.

As shown in FIG. 5B and FIG. 5C, in some examples, the second electrode 122 includes a portion 12201 located within the accommodating space 103, and of course, it may further include a portion 12202 not located within the accommodating space 103. In other examples, the second electrode 122 is located within the accommodating space 103 and is completely accommodated in the accommodating space 103.

As shown in FIG. 5B and FIG. 5C, in some examples, a protective layer 105 may be further provided on a side of the second electrode 122 that is away from the first base substrate 101. For the protective layer 105, the foregoing description may be referred to, and no details will be repeated here.

In the example of the present disclosure, the black matrix may be formed by forming a film layer and then patterning the film layer, or may also be formed in other modes.

Figure 5D:
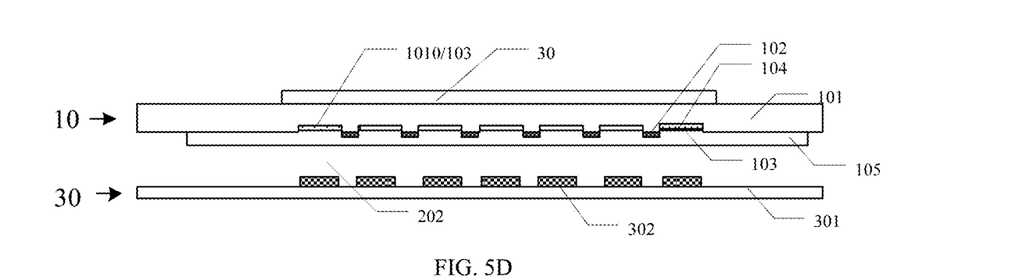
FIG. 5D is a schematic diagram of a spectrometer provided by another example of the present disclosure.

FIG. 5D is a schematic diagram of a spectrometer provided by another example of the present disclosure. As shown in FIG. 5D, in some examples, the accommodating space 103 is formed by removing a portion of the first base substrate 101.

As shown in FIG. 5D, in some examples, the accommodating space 103 on the first base substrate 101 is a recessed portion 1010 formed by removing a portion of the first base substrate 101, and the recessed portion 1010 is the accommodating space 103. The quantum dot light emitting unit 104 is located within the recessed portion 1010. As shown in FIG. 5D, the black matrix 102 may be provided on a portion of the first base substrate 101 that is located between adjacent recessed portions 1010. The black matrix 102 may prevent a crosstalk problem of light of different wavelengths emitted by the quantum dot light emitting units 104. For example, the black matrix 102 may be formed after the quantum dot layer 14 is formed, and the protective layer 105 may be formed after the black matrix 102 is formed. Alternatively, the black matrix 102 may be formed on the protective layer 105. For example, a projection of the black matrix 102 on the first base substrate 101 is located between adjacent quantum dot light emitting units 104.

Figure 6:
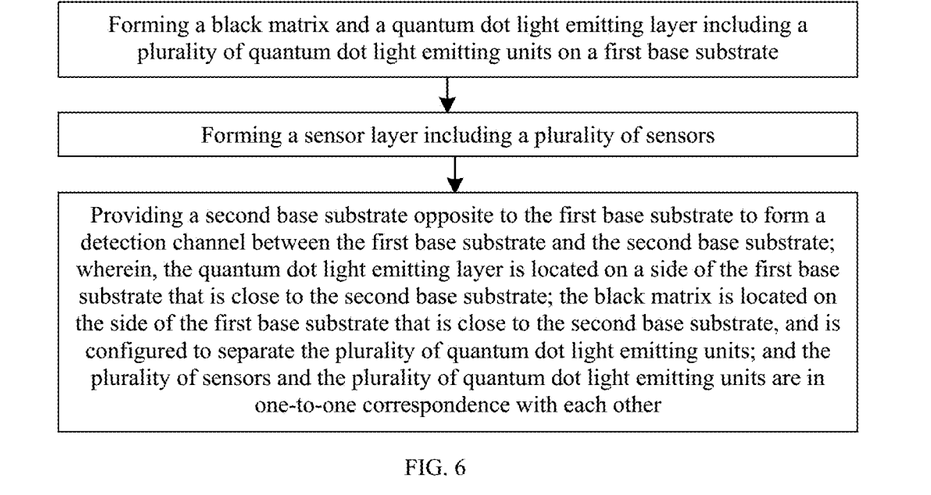
FIG. 6 is a flow chart of a fabrication method of a spectrometer provided by an example of the present disclosure.

FIG. 6 is a flow chart of a fabrication method of a spectrometer provided by an example of the present disclosure. The method comprises: forming a black matrix and a quantum dot light emitting layer including a plurality of quantum dot light emitting units on a first base substrate; forming a sensor layer including a plurality of sensors; and providing a second base substrate opposite to the first base substrate to form a detection channel between the first base substrate and the second base substrate; wherein, the quantum dot light emitting layer is located on a side of the first base substrate that is close to the second base substrate; the black matrix is located on the side of the first base substrate that is close to the second base substrate, and is configured to separate the plurality of quantum dot light emitting units; and the plurality of sensors and the plurality of quantum dot light emitting units are in one-to-one correspondence with each other.

The fabrication method of a spectrometer provided by at least one example of the present disclosure may be favorable for mass production. The example of the present disclosure may provide a low-cost, mass-producible, high-precision miniature spectrometer. The spectrometer provided by the example of the present disclosure may be used for detection and labelling in physical, biological, and chemical fields such as spectrum detection, substance analysis, labelling, molecular diagnostics, food quarantine, and bacterial classification.

For example, the forming a black matrix and a quantum dot light emitting layer including a plurality of quantum dot light emitting units on a first base substrate includes: forming the black matrix including a plurality of accommodating spaces on the first base substrate; and dripping a quantum dot solution into each of the plurality of accommodating spaces, heating to remove a substance to be removed from the quantum dot solution, to obtain the quantum dot light emitting layer.

For example, the dripping a quantum dot solution into each of the plurality of accommodating spaces includes: forming a solution of quantum dots that can be excited to generate light of different wavelengths, and respectively dripping the solution of quantum dots that can be excited to generate light of different wavelengths into a corresponding accommodating space.

For example, after the quantum dot solution is dripped into each of the plurality of accommodating spaces, it is heated by using a single heating process to remove the substance to be removed from the quantum dot solution. That is, a process of dripping the quantum dot solution in the plurality of accommodating spaces is completed firstly, and then heating is performed once to obtain the quantum dot light emitting layer.

For example, quantum dot materials of different sizes are dissolved in a dispersant to prepare the quantum dot solution. For example, the dispersant includes an organic solvent or water. The quantum dot solution is dripped into the accommodating space of the black matrix, and heated to remove the substance to be removed from the quantum dot solution, to obtain a quantum dot light emitting unit within the accommodating space. Quantum dot structures of different sizes may be excited by backlight or electricity to emit light of different wavelengths.

For example, colloidal or water-soluble quantum dots may be adopted to facilitate batch dripping into the accommodating space. The quantum dot material may be a water-soluble quantum dot structure synthesized by CdZnSe/ZnS, or may also be a colloidal quantum dot structure such as CdS or CdSe or ZnS dissolved in organic matter. For example, CdS or CdSe may be dissolved in organic matter to implement different wavelengths of transmitted light. The material of the quantum dot is not limited thereto, as long as it satisfies that light emission in different wavelength bands is adjustable by controlling the material or the size of the quantum dot.

In at least one example of the present disclosure, quantum dots may be adopted to emit light of different wavelengths; and electroluminescence or photoluminescence may be adopted to make the quantum dot light emitting layer emit light, so as to obtain the miniature spectrometer.

FIG. 7A to FIG. 7G show flow charts of a fabrication method of a spectrometer, which will be described in detail hereinafter.

Figure 7A:
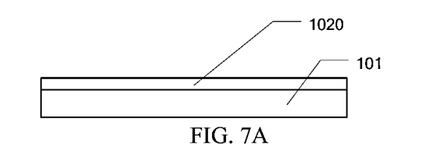
FIG. 7A to FIG. 7G show flow charts of a fabrication method of a spectrometer.

As shown in FIG. 7A, a black matrix thin film 1020 is formed on a first base substrate 101.

Figure 7B:
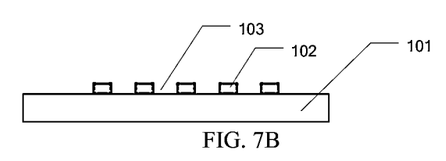

As shown in FIG. 7B, the black matrix thin film 1020 is patterned to form a black matrix 102. The black matrix 102 is configured to form a plurality of accommodating spaces 103. For example, the patterning may include a photoetching process or a nanometer imprinting method. For example, when the black matrix thin film 1020 adopts photoresist containing a black dye, an accommodating space 103 for accommodating a quantum dot solution may be pressed out on the photoresist by using the nanometer imprinting method. For example, the photoetching process includes exposure and development, to form the black matrix 102. For example, the black matrix thin film 1020 may be exposed with a mask, and developed to form the black matrix 102.

Figure 7C:
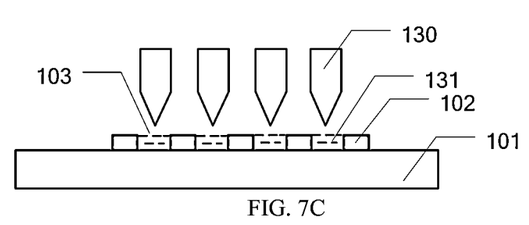

As shown in FIG. 7C, a quantum dot solution containing quantum dots of different sizes is prepared and injected into a corresponding accommodating space 103. For example, the quantum dot solution may be dripped into the accommodating space 103 by means of inkjet printing, and a quantum dot solution layer 131 may be formed in the accommodating space 103. For example, quantum dot light emitting units that emit light of a same wavelength may have the quantum dot solution dripped at a same time, and so on, until the quantum dot solution is dripped into all the accommodating spaces. FIG. 7C shows an injection structure 130 for injecting the quantum dot solution into the accommodating space 103.

Figure 7D:
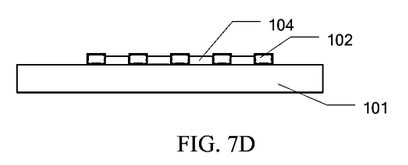

As shown in FIG. 7D, heating is performed to remove a substance to be removed from the quantum dot solution, so as to form a quantum dot light emitting unit 104 in each accommodating space. The plurality of quantum dot light emitting units 104 constitute the quantum dot light emitting layer 14.

Figure 7E:
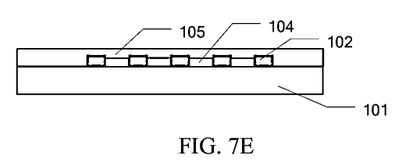

As shown in FIG. 7E, a protective layer 105 is formed on the quantum dot light emitting layer 14.

Figure 7F:
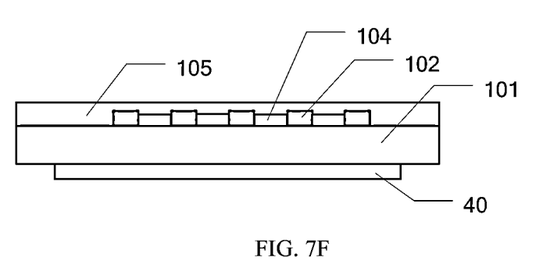

As shown in FIG. 7F, a light source portion 40 is formed on a side of the first base substrate 101 that is not provided with the black matrix 102, to obtain a first substrate 10.

Figure 7G:
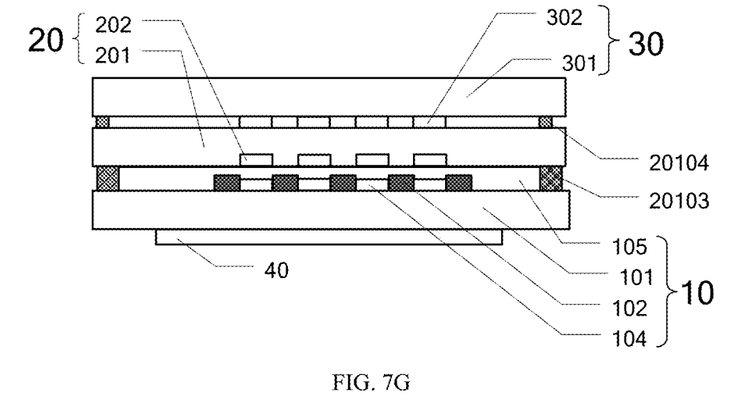

As shown in FIG. 7G, a plurality of sensors 302 are formed on a third base substrate 301 to form a third substrate 30; a detection channel 202 is formed in a second base substrate 201 to form a second substrate 20; the first substrate 10 and the second substrate 20 are provided opposite to each other; and the second substrate 20 is placed between the first substrate 10 and the third substrate 30 to obtain the spectrometer. For example, the first substrate 10 and the second substrate 20 may be packaged by a first sealant 20103, and the second substrate 20 and the third substrate 30 may be packaged by a second sealant 20104.

For example, in order to facilitate accurate alignment of the accommodating spaces of the first substrate 10 and the sensors of the third substrate 30, alignment marks may be respectively made on the first base substrate 101 and the second base substrate 201, to facilitate accurate alignment.

FIG. 7A to FIG. 7G illustrate with a case where the quantum dot solution is dripped into each accommodating space, and then heated to form the quantum dot light emitting layer as an example.

In other examples, a first quantum dot solution may be dripped into a part of the accommodating spaces, then heated for a first time to form quantum dot light emitting units in the part of the accommodating spaces; a second quantum dot solution is dripped into a part of the accommodating spaces, then heated for a second time to form quantum dot light emitting units in the part of the accommodating spaces; and so on, until fabrication of quantum dot light emitting units in all the accommodating spaces is completed. For example, the first quantum dot solution and the second quantum dot solution differ in sizes of quantum dots, so as to respectively form quantum dot light emitting units that emit light of different wavelengths. For example, the first quantum dot solution and the second quantum dot solution adopts quantum dots of different materials, so as to respectively form quantum dot light emitting units that emit light of different wavelengths.

FIG. 7A to FIG. 7G illustrate the fabrication method by taking a spectrometer comprising a backlight as an example. For example, by using the method shown in FIG. 7A to FIG. 7G, the spectrometer shown in FIG. 1 may be formed. Hereinafter, different parts of fabrication methods of other forms of spectrometers will be described.

With respect to the spectrometer in the optical waveguide form, for example, as shown in FIG. 5A, the black matrix 102 configured to form the plurality of accommodating spaces 103 may be formed on the first base substrate 101; next, the first base substrate 101 is etched with the black matrix 102 as a mask, to form the light extraction structure 1011; and then subsequent fabrication is performed.

With respect to the spectrometer in the electroluminescence form, for example, as shown in FIG. 5B, the first electrode 121 may be formed on the first base substrate 101; next, the black matrix 102 is formed on the first electrode 121; then the quantum dot light emitting unit 104 is formed within the accommodating space 103 of the black matrix 102; and the second electrode 122 is formed on the quantum dot light emitting unit 1034.

For example, an inlet and an outlet may be provided on the second base substrate 201 to facilitate a liquid to flow into and out of the detection channel 202. The inlet and the outlet are not shown in the figures.

In at least one example of the present disclosure, the accommodating space formed by the black matrix is used to hold quantum dots of different sizes, to implement light emission at different wavelengths; and electroluminescence or photoluminescence is used to implement a glass-based miniature spectrometer.

It should be noted that, for clarity, the thickness of layers or areas in the accompanying drawings of the embodiments of the present disclosure is enlarged. It should be understood that when an element such as a layer, a film, an area or a substrate is referred to be disposed "on" or "beneath" another element, the element may be "directly" disposed "on" or "beneath" another element, or an intermediate element may be provided.

The features in the same embodiment or different embodiments of the present disclosure may be mutually combined without conflict.

The foregoing is only the preferred embodiments of the present invention and not intended to limit the scope of protection of the present disclosure. Any change or replacement that may be easily thought of by those skilled in the art within the technical scope disclosed by the present disclosure shall fall within the scope of protection of the present disclosure. Therefore, the scope of protection of the present invention shall be defined by the appended claims.

The invention claimed is:

1. A spectrometer, comprising:
   a first base substrate;
   a second base substrate opposite to the first base substrate;
   a detection channel between the first base substrate and the second base substrate and configured to accommodate or pass a liquid to be detected;
   a quantum dot light emitting layer on a side of the first base substrate that is close to the second base substrate, and including a plurality of quantum dot light emitting units, wherein an orthogonal projection of the plurality of quantum dot light emitting units on the first base substrate falls within an orthogonal projection of the detection channel on the first base substrate;
   a black matrix on the side of the first base substrate that is close to the second base substrate, and configured to separate the plurality of quantum dot light emitting units; and
   a sensor layer, including a plurality of sensors in one-to-one correspondence with the plurality of quantum dot light emitting units,
   the quantum dot light emitting layer protrudes from a surface of the first base substrate, and protrudes toward the second base substrate, the detection channel in which fluid to be investigated is located is in the second base substrate, and the plurality of sensors are located between the second base substrate and a third base substrate, the third base substrate is opposite to the second base substrate and located on a side of the second base substrate away from the first base substrate, and the sensor layer and the quantum dot light emitting layer are located in a same side of the detection channel.

2. The spectrometer according to claim 1, wherein the black matrix is configured to form a plurality of accommodating spaces each of which is configured to accommodate one of the plurality of quantum dot light emitting units; and in a direction perpendicular to the first base substrate, the black matrix has a size larger than or equal to that of the quantum dot light emitting layer.

3. The spectrometer according to claim 2, further comprising a first electrode on a side of the quantum dot light emitting units that is away from the second base substrate and a second electrode on a side of the quantum dot light emitting unit that is close to the second base substrate; and the first electrode and the second electrode are configured to be applied with different voltages to excite the quantum dot light emitting units to emit light.

4. The spectrometer according to claim 3, wherein the black matrix is located between the first electrode and the second electrode.

5. The spectrometer according to claim 4, wherein the second electrode includes a portion within the accommodating space.

6. The spectrometer according to claim 1, further comprising a protective layer on a side of the quantum dot light emitting layer that is away from the first base substrate, wherein the protective layer is configured to protect the quantum dot light emitting layer.

7. The spectrometer according to claim 6, wherein, in the direction perpendicular to the first base substrate, a sum of sizes of the protective layer and the quantum dot light emitting layer is larger than or equal to the size of the black matrix.

8. The spectrometer according to claim 1, wherein the quantum dot light emitting layer is formed by adopting at least one selected from the group consisting of quantum dots of different types and quantum dots of different sizes.

9. The spectrometer according to claim 1, wherein the sensor layer is on a side of the detection channel that is away from the quantum dot light emitting layer, and an orthogonal projection of the sensor layer on the first base substrate falls within an orthogonal projection of the quantum dot light emitting layer on the first base substrate.

10. The spectrometer according to claim 1, wherein the sensor layer is on a side of the detection channel that is close to the quantum dot light emitting layer, and an orthogonal projection of the sensor layer on the first base substrate falls within an orthogonal projection of the black matrix on the first base substrate.

11. The spectrometer according to claim 1, further comprising a light source portion configured to provide excitation light irradiated onto the quantum dot light emitting layer to excite the quantum dot light emitting layer to emit light.

12. The spectrometer according to claim 11, wherein the light source portion is on a side of the first base substrate that is away from the second base substrate, and includes a backlight of direct-lit type; and a reflective layer is provided on a side of the backlight of direct-lit type that is close to the first base substrate.

13. The spectrometer according to claim 11, wherein the light source portion is on a side of the first base substrate that is away from the second base substrate, and includes a backlight of edge-lit type; and a reflective layer is provided on a side of the backlight of the edge-lit type that is away from the first base substrate.

14. The spectrometer according to claim 11, wherein the light source portion includes a light source on a side face of the first base substrate; the first base substrate is a glass substrate and constitutes an optical waveguide; the first base substrate further includes a plurality of light extraction structures in one-to-one correspondence with the plurality of quantum dot light emitting units; and the plurality of light extraction structures are located on the side of the first base substrate that is close to the second base substrate.

15. The spectrometer according to claim 14, wherein the light extraction structure includes a blind hole.

16. A fabrication method of a spectrometer, comprising:
    forming a black matrix and a quantum dot light emitting layer including a plurality of quantum dot light emitting units on a first base substrate;
    forming a sensor layer including a plurality of sensors; and
    providing a second base substrate opposite to the first base substrate to form a detection channel between the first base substrate and the second base substrate and configured to accommodate or pass a liquid to be detected,
    wherein the quantum dot light emitting layer is on a side of the first base substrate that is close to the second base substrate; the black matrix is on the side of the first base substrate that is close to the second base substrate, and is configured to separate the plurality of quantum dot light emitting units; and the plurality of sensors and the plurality of quantum dot light emitting units are in one-to-one correspondence with each other, and an orthogonal projection of the plurality of quantum dot light emitting units on the first base substrate falls within an orthogonal projection of the detection channel on the first base substrate,
    the quantum dot light emitting layer protrudes from a surface of the first base substrate, and protrudes toward the second base substrate, the detection channel in which fluid to be investigated is located is in the second base substrate, and the plurality of sensors are located between the second base substrate and a third base substrate, the third base substrate is opposite to the second base substrate and located on a side of the second base substrate away from the first base substrate, and the sensor layer and the quantum dot light emitting layer are located in a same side of the detection channel.

17. The method according to claim 16, wherein forming the black matrix and the quantum dot light emitting layer including the plurality of quantum dot light emitting units on the first base substrate includes:
    forming the black matrix including a plurality of accommodating spaces on the first base substrate; and
    dripping a quantum dot solution into each of the plurality of accommodating spaces, heating to remove a substance to be removed from the quantum dot solution, to obtain the quantum dot light emitting layer.

18. The method according to claim 17, wherein dripping the quantum dot solution into each of the plurality of accommodating spaces includes: forming a solution of quantum dots that can be excited to generate light of different wavelengths, and dripping the solution of quantum dots that can be excited to generate light of different wavelengths into the respective corresponding accommodating spaces.

19. The method according to claim 17, wherein, after the quantum dot solution is dripped into each of the plurality of accommodating spaces, the substance to be removed is removed from the quantum dot solution by a single heating process.

20. A spectrometer, comprising:
- a first base substrate;
- a second base substrate opposite to the first base substrate;
- a detection channel between the first base substrate and the second base substrate and configured to accommodate or pass a liquid to be detected;
- a quantum dot light emitting layer on a side of the first base substrate that is close to the second base substrate, and including a plurality of quantum dot light emitting units, wherein an orthogonal projection of the plurality of quantum dot light emitting units on the first base substrate falls within an orthogonal projection of the detection channel on the first base substrate;
- a black matrix on the side of the first base substrate that is close to the second base substrate, and configured to separate the plurality of quantum dot light emitting units; and
- a sensor layer, including a plurality of sensors in one-to-one correspondence with the plurality of quantum dot light emitting units,
- the quantum dot light emitting layer protrudes from a surface of the first base substrate, and protrudes toward the second base substrate, the detection channel in which fluid to be investigated is located is in the second base substrate, and the plurality of sensors are located between the second base substrate and a third base substrate, the third base substrate is opposite to the second base substrate and located on a side of the second base substrate away from the first base substrate, and the third base substrate is located between the first base substrate and the second base substrate in a direction perpendicular to the first base substrate.

* * * * *